United States Patent [19]
Landis

[11] Patent Number: 5,772,031
[45] Date of Patent: Jun. 30, 1998

[54] PACKAGE FOR AN ELONGATED MEDICAL PRODUCT

[75] Inventor: Larry R. Landis, Warsaw, Ind.

[73] Assignee: Zimmer, Inc., Warsaw, Ind.

[21] Appl. No.: 601,932

[22] Filed: Feb. 15, 1996

[51] Int. Cl.⁶ .................................................. B65D 85/24
[52] U.S. Cl. ........................ 206/438; 206/363; 206/471; 206/565; 206/814
[58] Field of Search .................................. 206/438, 363, 206/364, 365, 814, 588, 467, 468, 471, 488, 564–565; 220/532

[56] References Cited

U.S. PATENT DOCUMENTS

| | | | |
|---|---|---|---|
| 2,018,651 | 10/1935 | Bates ........................................ | 206/564 |
| 3,869,043 | 3/1975 | Warner et al. . | |
| 4,005,776 | 2/1977 | Seeley ..................................... | 206/364 |
| 4,324,331 | 4/1982 | Ignasiak . | |
| 4,750,619 | 6/1988 | Cohen et al. . | |
| 4,753,345 | 6/1988 | Goodsir et al. ......................... | 206/365 |
| 5,062,800 | 11/1991 | Niznick . | |
| 5,082,112 | 1/1992 | Dunklee . | |
| 5,090,571 | 2/1992 | Walker . | |
| 5,133,454 | 7/1992 | Hammer . | |
| 5,148,920 | 9/1992 | Walker . | |
| 5,193,679 | 3/1993 | White . | |
| 5,201,825 | 4/1993 | Artusi et al. . | |
| 5,284,632 | 2/1994 | Kudla et al. ............................ | 206/363 |
| 5,339,955 | 8/1994 | Horan et al. ............................ | 206/364 |
| 5,351,822 | 10/1994 | Sinn . | |
| 5,386,908 | 2/1995 | Sinn . | |
| 5,392,909 | 2/1995 | Hackett . | |
| 5,441,707 | 8/1995 | Lewis et al. . | |
| 5,482,067 | 1/1996 | Wittrock et al. ........................ | 206/363 |
| 5,492,671 | 2/1996 | Krafft ..................................... | 206/363 |
| 5,520,939 | 5/1996 | Wells ...................................... | 206/471 |
| 5,540,901 | 7/1996 | Riley ...................................... | 206/438 |

OTHER PUBLICATIONS

Photographs—Prior Art Cavity—Zimmer—No date available.
Photographs—Prior Art Cavity—Synthes—No date available.
Photographs—Prior Art Cavity—Richards Medical Company—No date available.

*Primary Examiner*—Paul T. Sewell
*Assistant Examiner*—Luan K. Bui
*Attorney, Agent, or Firm*—Cary R. Reeves

[57] ABSTRACT

A package includes a cavity having a series of cavity slots transverse to the cavity's longitudinal axis. These slots permit a pair of stop plugs to be positioned to receive products of different lengths. Each stop plug has four lateral lugs for engaging the cavity slots to resist linear and rotational displacement of the stop plug. Each plug has bottom, end, and side walls to isolate the product end from the cavity. In addition a pair of fingers extending from the stop plug elastically grips the product to further restrain product movement. The fingers can flex to accommodate different sizes of products. A retainer snaps onto the cavity to close it. The retainer includes a retainer stop at each end that extends into the cavity and prevents the retainer from shifting even if the retainer is lifted due to product pressure against the retainer during shipping. The retainer also includes a pair of product restraints extending into the cavity to limit motion of the product toward the retainer. The product restraints are shaped to also provide finger wells for aiding the removal of the retainer when the package is opened. Retaining slots in the retainer cooperate with a top lug on the stop plug to further hold the stop plug in place when the package is assembled.

7 Claims, 5 Drawing Sheets

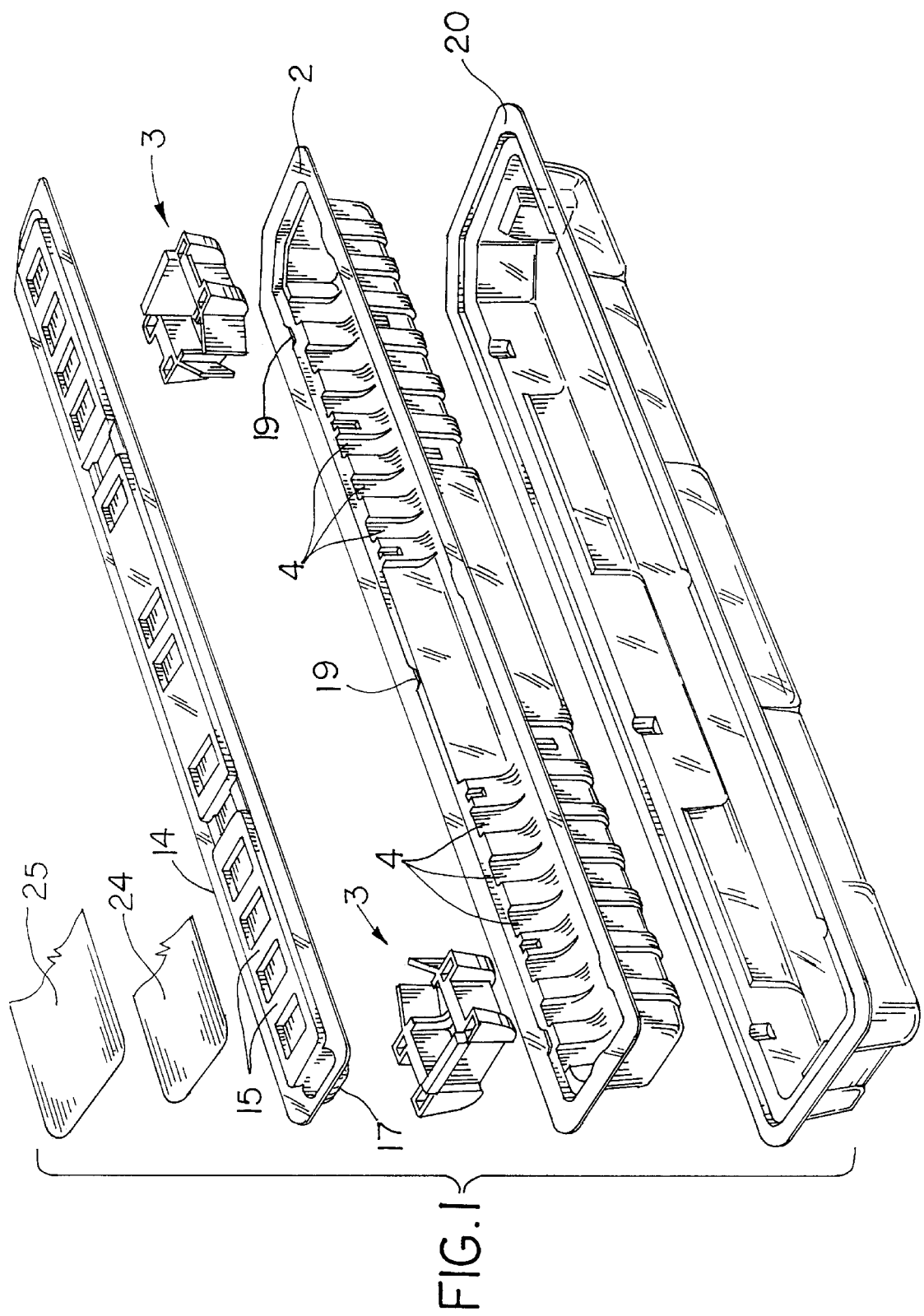

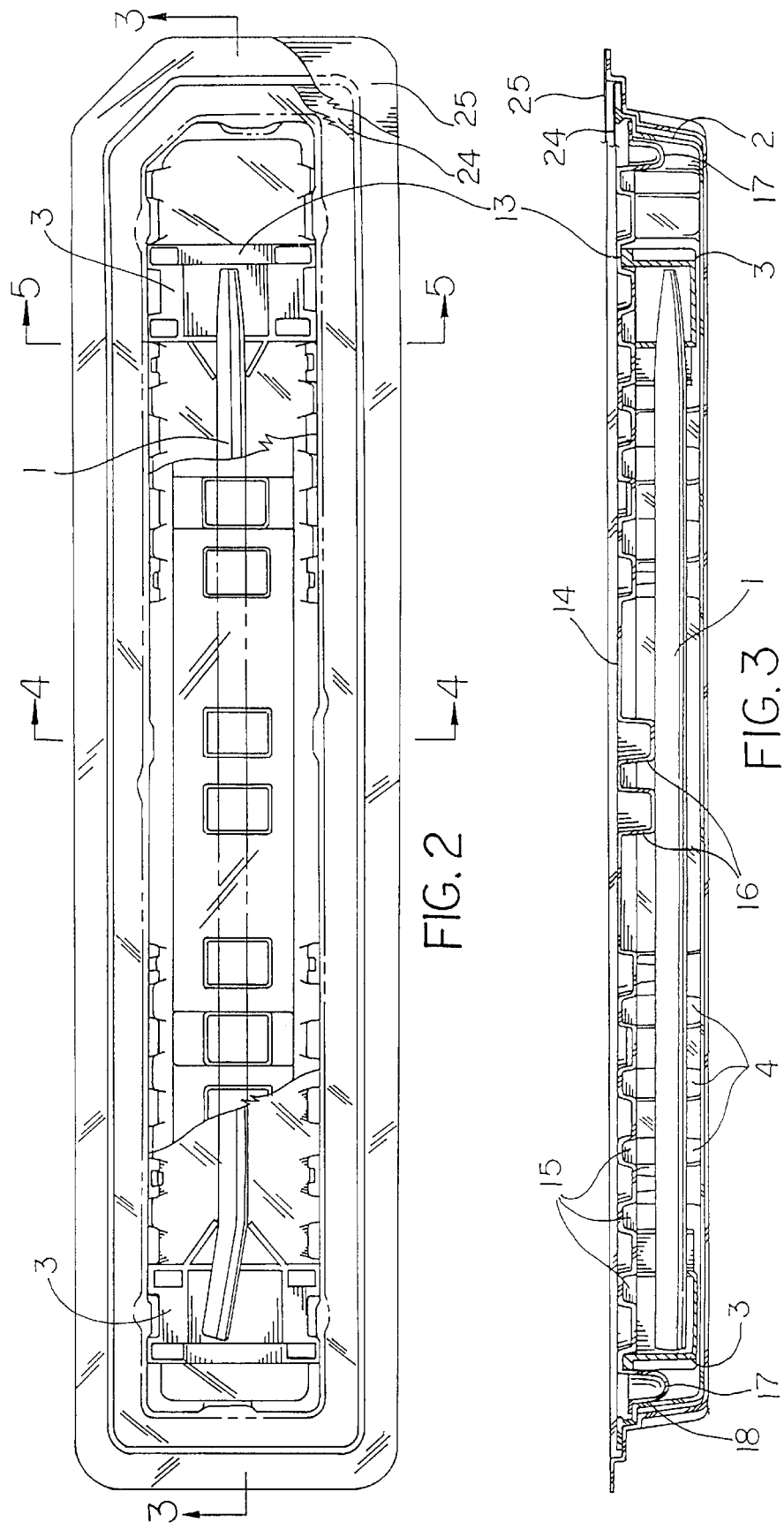

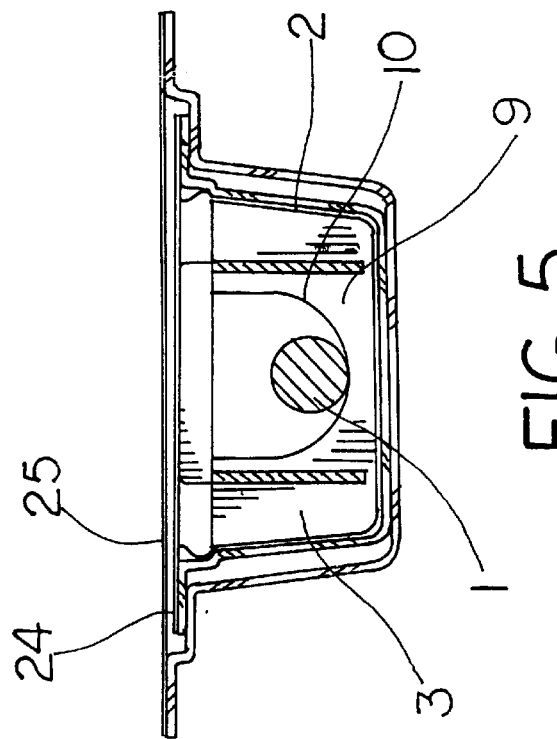
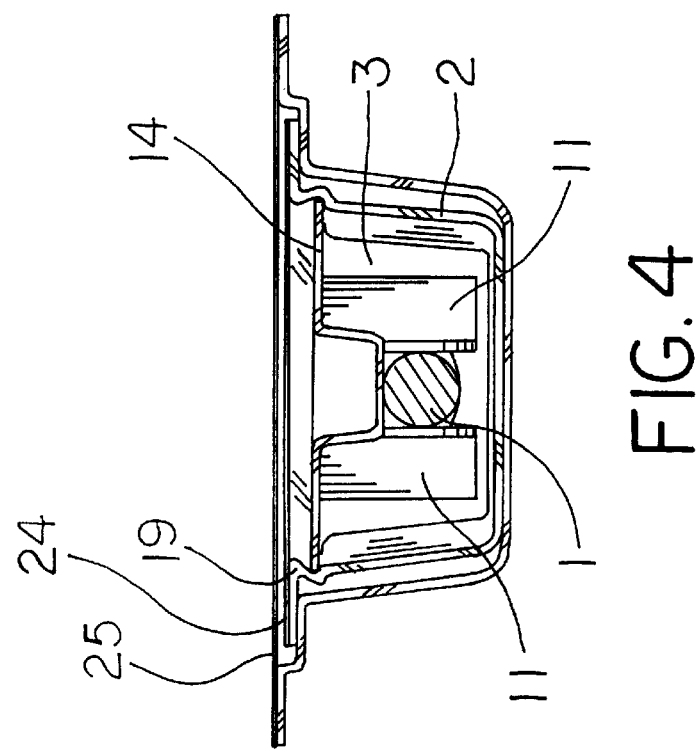

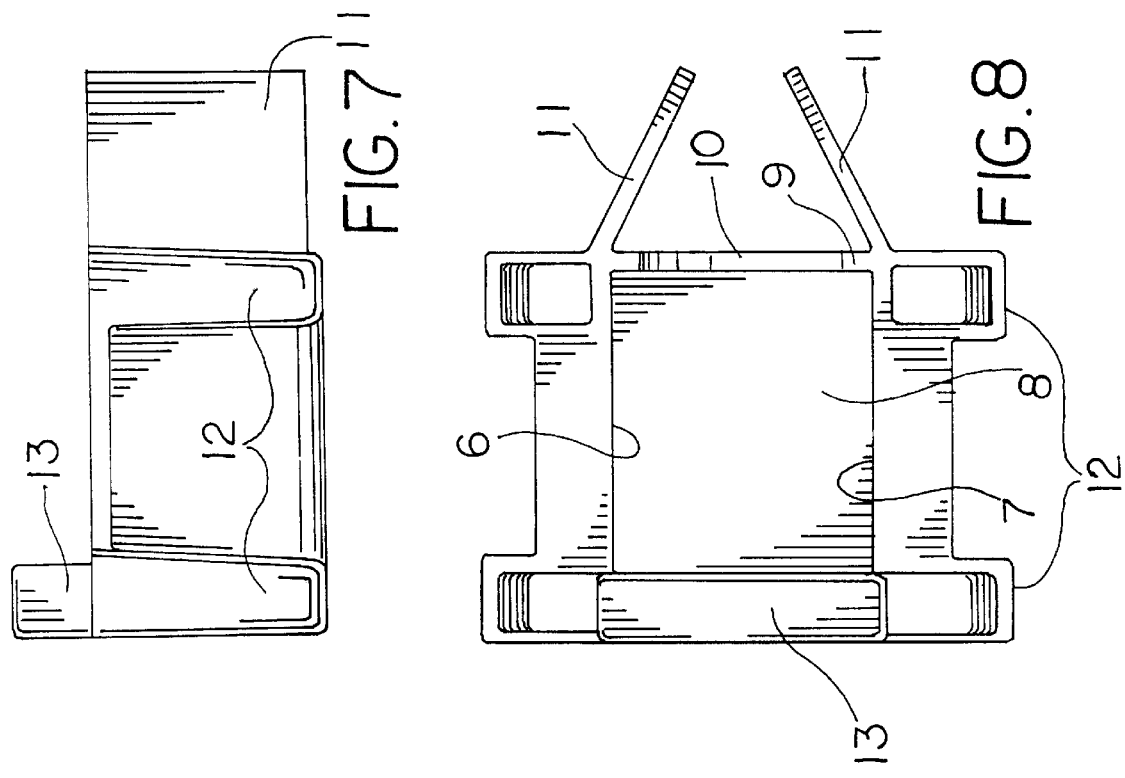
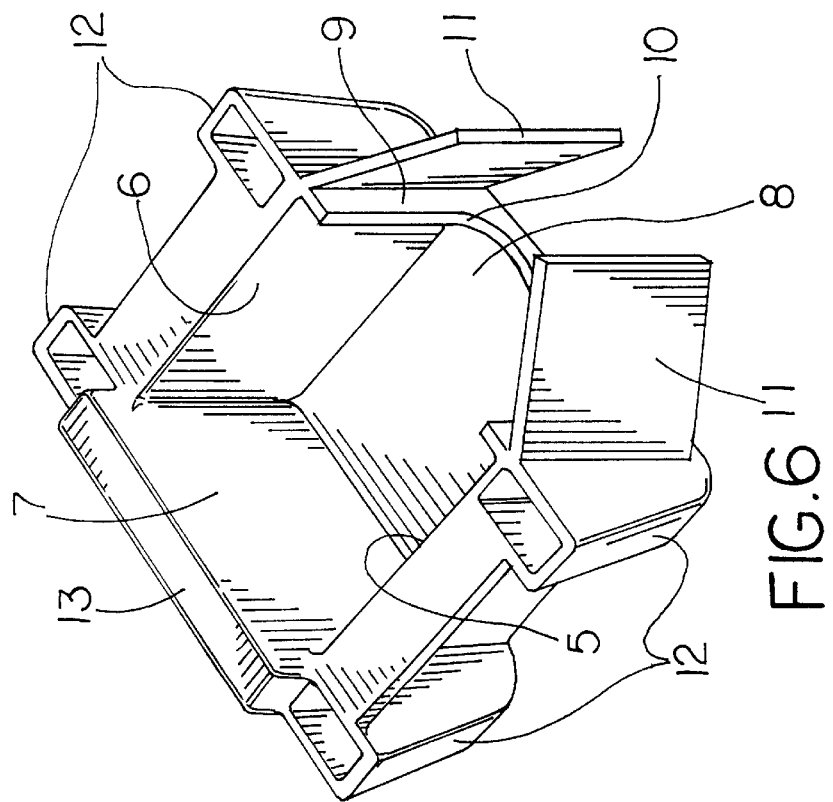

5,772,031

PACKAGE FOR AN ELONGATED MEDICAL PRODUCT

BACKGROUND OF THE INVENTION

The present invention relates to a package for medical products and more particularly to a package especially suited for sterile elongated medical products.

A sterile medical product requires a package that allows the product to be sterilized and that then maintains the sterile environment inside the package. A typical prior art package includes a thermoformed cavity defining a space for the product, a rigid retainer overlying the product, and a flexible cover heat sealed to the rim of the cavity. This kind of prior art package sometimes fails to maintain sterility because of damage to the package that creates openings which allow pathogens to enter. Typically this damage is precipitated by shipping or other handling of the package. Often the damage results from the product itself impacting against the package interior. Typical failure modes include the product puncturing the end of the package in a severe impact such as occurs when the package is dropped; the product abrading against the package and wearing a hole through the package when it is vibrated such as occurs during shipping; and the product pressing against the retainer and causing the retainer to slip between the cavity rim and the flexible cover when the package is inverted and shaken thus causing the flexible cover to peel away from the rim. These failure modes are aggravated in the case of heavy elongated medical products such as metal implants and instruments.

In addition to being durable, a surgical implant package should be economical. The materials used in the package should be inexpensive and easily assembled. Furthermore, the same package should accommodate as many different implants as possible to enable economies of scale in manufacturing many of the same package as opposed to manufacturing fewer of several different packages.

Prior packages have attempted to address these requirements. U.S. Pat. 4,324,331 issued to Ignasiak teaches a storage cavity for surgical implements having longitudinally spaced areas for receiving protective plugs. The package addresses the need for durability with the protective plugs which help to prevent the implement from puncturing the ends of the cavity. The package design addresses the need for economy because the plugs can be positioned selectively in the longitudinally spaced areas to accommodate implements of different lengths.

SUMMARY OF THE INVENTION

The present invention improves on the prior art by providing a package for a medical product that provides highly puncture resistant stop plugs for preventing the product from being propelled longitudinally through the package end walls. The present invention also isolates the product from the package walls to prevent abrasive rupturing of the package walls. In addition, the present package is configured to prevent the retainer from slipping between the cavity rim and the flexible cover. Finally, the package of the present invention is economical since it is adjustable to accommodate several different product lengths using the same package.

The package of the present invention includes a cavity having a series of cavity slots transverse to the cavity's longitudinal axis. These slots permit a pair of stop plugs to be positioned to receive products of different lengths. Each stop plug has four lateral lugs for engaging the cavity slots to resist linear and rotational displacement of the stop plug. Each plug has bottom, end, and side walls to isolate the product end from the cavity. In addition a pair of fingers extending from the stop plug elastically grips the product to further restrain product movement. The fingers can flex to accommodate different sizes of products. A retainer snaps onto the cavity to close it. The retainer includes a retainer stop at each end that extends into the cavity and prevents the retainer from shifting even if the retainer is lifted due to product pressure against the retainer during shipping. The retainer also includes a pair of product restraints extending into the cavity to limit motion of the product toward the retainer. The product restraints are shaped to also provide finger wells for aiding the removal of the retainer when the package is opened. Retaining slots in the retainer cooperate with a top lug on the stop plug to further hold the stop plug in place when the package is assembled. These features of the product and others are more fully described in the figures and the detailed description of the invention.

BRIEF DESCRIPTION OF THE DRAWINGS

FIG. 1 is an exploded perspective view of an embodiment of the present invention.

FIG. 2 is a top plan partial cut-away view of the embodiment of FIG. 1.

FIG. 3 is a front partial-section view taken along lines 3—3 of FIG. 2.

FIG. 4 is a side section view taken along lines 4—4 of FIG. 2.

FIG. 5 is a side section view taken along lines 5—5 of FIG. 2.

FIG. 6 is a perspective view of the stop plug of FIG. 1.

FIG. 7 is a front plan view of the stop plug of FIG. 1.

FIG. 8 is a top plan view of the stop plug of FIG. 1.

DETAILED DESCRIPTION OF THE INVENTION

Figure 9:
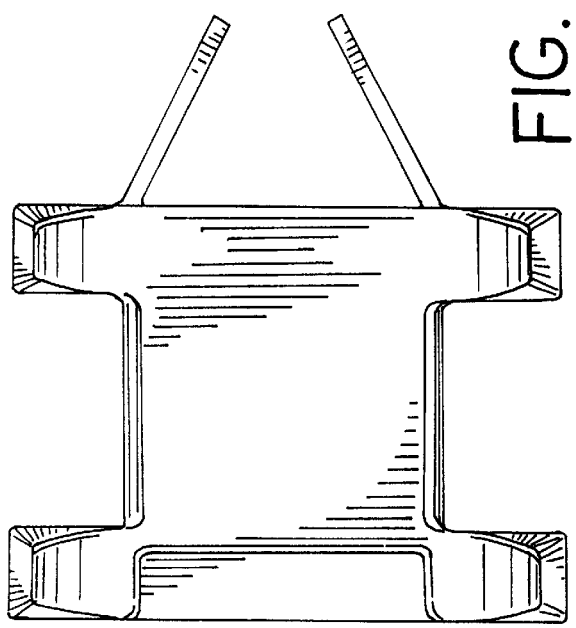
FIG. 9 is a bottom plan view of the stop plug of FIG. 1.
Figure 11:
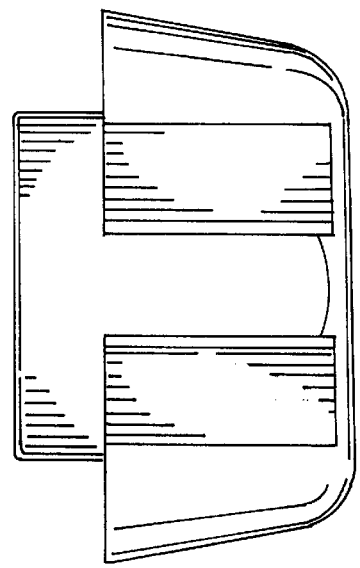
FIG. 11 is an end plan view of the stop plug of FIG. 1 opposite the view of FIG.10.
Figure 10:
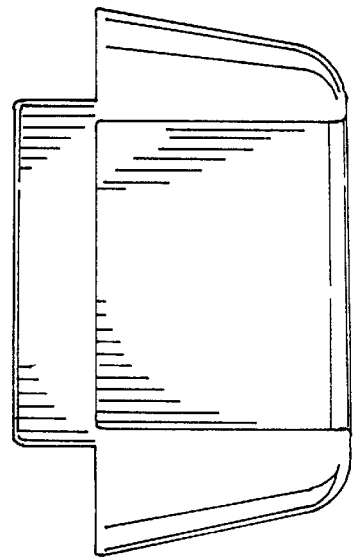
FIG. 10 is an end plan view of the stop plug of FIG. 1.

Referring to FIGS. 1–11, a package for an elongated product 1 includes an inner cavity 2 and a pair of stop plugs 3. The inner cavity 2 comprises a container having surrounding side and end walls, a bottom wall and an open top. The inner cavity has a longitudinal axis parallel to the side walls. The inner cavity 2 contains a plurality of cavity slots 4 formed in the side walls transverse to the longitudinal axis for receiving a portion of the stop plug 3. Preferably the inner cavity 2 contains several pairs of opposed cavity slots 4 extending along the length of the inner cavity 2 at least at each end to permit positioning the stop plugs 3 to accommodate products 1 having different lengths.

The stop plugs 3 are configured to isolate the ends of an elongated product 1 from the inner cavity 2. Each stop plug 3 includes opposed side walls 5 and 6, an end wall 7 and a bottom 8 thus forming an enclosure closed on at least the sides, end, and bottom. Opposite the end wall 7 is a front wall 9. The front wall 9 contains a U-shaped opening 10. The lower portion of the U-shaped opening 10 can extend above the bottom 8 to support the product (as shown in FIGS. 3, 5 and 6) or it can be at the same level or below the bottom 8 so that the product rests on the bottom 8. The top of the stop plug 3 is open to receive the end of the product 1. Two fingers 11 extend from the front wall 9 adjacent the U-shaped opening 10 outwardly away from the stop plug 3. The fingers 11 converge toward one another so that they are able to press against or grip the product 1. Preferably they converge toward the longitudinal axis. Four lateral lugs 12 extend from the side walls 5 and 6 to engage the cavity slots 4 in the inner cavity 2. A top lug 13 extends upwardly from the end wall to engage a portion of a retainer 14. Preferably the stop plug 3 is made of a rigid, abrasion and puncture resistant polymer. The polymer is also chosen so that the fingers 11 are elastically deformable over relatively small distances and plastically deformable without breaking over larger distances. This construction ensures that a product end will not wear through or pierce the stop plug and it allows the fingers to be plastically deformed to easily accommodate different sizes of product 1 while still retaining elasticity to releasably grip the product 1. It has been found that injection molded polyethylene provides the desired performance.

The retainer 14 is adapted to fit onto the inner cavity 2 to close the open top of the inner cavity 2. The retainer 14 includes retainer slots 15 formed along its length transverse to the longitudinal axis. The retainer slots 15 receive the top lug 13 and correspond to and preferably align with the cavity slots 4. The retainer 14 also includes product restraints 16 which extend downwardly into the inner cavity 2 when the retainer 14 is positioned on the inner cavity 2. On large and heavy implants, it is preferable that the product restraints 16 extend into the cavity far enough to occupy more than half the distance between the retainer 14 and the product 1 so as to restrict the amount of displacement the product 1 can undergo between the bottom of the inner cavity 2 and the retainer 14. Preferably the product restraints 16 are formed as hollow bulges in the retainer so that from the top a user can extend his fingers into the hollow interior of the product restraints to facilitate gripping and removing the retainer. The retainer 14 also preferably includes a retainer stop 17 formed at each end and extending into the inner cavity 2. The retainer stop 17 is preferably formed as an elongated projection oriented transverse to the longitudinal axis of the retainer 14 and inner cavity 2. The distance the retainer stop 17 extends into the inner cavity is greater than the distance the retainer 14 can rise when the package is assembled with an overlying flexible cover 24 adhered to the top of the inner cavity 2. In other words, if the product is inverted or impacted thereby causing the package contents to press the retainer above the top of the inner cavity 2 to the extreme limit of the flexible covering 24, the retainer stop 17 will still extend into the inner cavity 2. The retainer stop 17 presents a flat surface 18 to the end wall of the inner cavity 2 which prevents the retainer 14 from slipping sideways between the top of the cavity and the flexible covering 24. Finally, the inner cavity 2 preferably includes retainer snaps 19 positioned around the perimeter of its top to releasably, positively engage the retainer 14 by overlying it and hold it in engagement with the inner cavity 2.

In use, a pair of stop plugs 3 are selected and their fingers 11 are bent inwardly or outwardly to a position in which the product 1 can be readily inserted and in which the fingers 11 still will elastically grip the product 1. The pair of stop plugs 3 are then positioned in the inner cavity 2 at a spacing appropriate for the particular product 1. The lateral lugs 12 of the stop plugs 3 engage the cavity slots 4 to resist translation and rotation of the stop plugs 3. Next, the product 1 is pressed into the stop plugs 3 where it is gripped by the fingers 11 and where the product's 1 ends are enclosed by the side walls 5 and 6, end wall 7, and bottom wall 8. The retainer 14 is then snapped onto the inner cavity 2 so that the retainer snaps 19 engage the retainer 14. The top lug 13 engages the retainer slots 15 to further stabilize the stop plugs 3 and prevent them from tipping up in the inner cavity 2. The product restraints 16 extend downwardly into the inner cavity 2 to occupy more than half of the space between the retainer 14 and the product 1 so as to keep the product 1 in the lower portion of the inner cavity 2. With the product 1 thus positioned its ends are isolated from the inner cavity 2, its end to end motion is restricted by the adjustably fitted stop plugs 3, and its up and down motion is restricted by the product restraints 16. Therefore, the product 1 is unlikely rub through the package or to develop sufficient inertia to be projected through the package. To complete the package assembly, a flexible covering 24 is sealed to the top of the inner cavity 2 and the inner cavity 2 is placed within an outer cavity 20 which is likewise sealed with a flexible top covering 25.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A package for an elongated medical product having an end, the package comprising:

a cavity having surrounding side and end walls, a bottom wall and an open top, the cavity having a longitudinal axis parallel to the side walls, a cavity slot being formed in the side walls transverse to the longitudinal axis;

a stop plug having opposed side walls, an end wall, and a bottom thus forming a partial enclosure, a lug extending from the stop plug, the lug engaging the cavity slot to restrain the stop plug from motion along the longitudinal axis, the partial enclosure formed by the stop plug being engageable with the end of the product, wherein the stop plug further includes a front opposite the end wall, at least one finger extends from the front outwardly away from the stop plug, the finger converges toward the longitudinal axis so that it is able to press against the product, the finger being elastically deformable so that it can flex away from the longitudinal axis to allow the end of the product to be positioned in the stop plug and so that it will press against the product once the product is positioned.

2. The package of claim 1 further comprising at least two fingers extending from the front outwardly away from the stop plug, the fingers converging toward one another so that they are able to grip the product.

3. A package for an elongated medical product having an end, the package comprising:

a cavity having surrounding side and end walls a bottom wall and an open top, the cavity having a longitudinal axis parallel to the side walls, a cavity slot being formed in the side walls transverse to the longitudinal axis;

a stop plug having opposed side walls, an end wall, and a bottom thus forming a partial enclosure, a lug extending from the stop plug, the lug engaging the cavity slot to restrain the stop plug from motion along the longitudinal axis, the partial enclosure formed by the stop plug being engageable with the end of the product, and a retainer closing the open top of the cavity, the stop plug including a top lug extending upwardly from the stop plug and the retainer including a slot for engaging the top lug.

4. A package for an elongated medical product having an end, the package comprising:
- a cavity having surrounding side and end walls, a bottom wall and an open top, the cavity having a longitudinal axis parallel to the side walls, a plurality of cavity slots being formed in the side walls transverse to the longitudinal axis; and
- a stop plug having opposed side walls, a front, an end wall opposite the front, and a bottom thus forming a partial enclosure, a plurality of lugs extending from the stop plug, the lugs engaging the cavity slots to restrain the stop plug from motion along the longitudinal axis, at least two fingers extending from the front outwardly away from the stop plug, the fingers converging toward one another so that they are able to grip the product, the partial enclosure formed by the stop plug being engageable with the end of the product.

5. The package of claim 4 further comprising an elongated product contained therein and a retainer closing the open top of the cavity, the retainer including a product restraint that extends downwardly into the cavity at least half the distance between the retainer and the product.

6. The package of claim 5 wherein the stop plug includes a top lug extending upwardly from the stop plug and the retainer includes a slot for engaging the top lug.

7. In combination:
- a cavity having surrounding side and end walls, a bottom wall and an open top, the cavity having a longitudinal axis parallel to the side walls, a cavity slot formed in the side walls transverse to the longitudinal axis;
- a stop plug having opposed side walls, an end wall, and a bottom forming a partial enclosure, a lug extending from the stop plug, the lug engaging the cavity slot to restrain the stop plug from motion along the longitudinal axis, the end wall of the stop plug being transverse to the longitudinal axis and parallel to one of the cavity end walls,
- an elongated medical implant having an end, the end of the elongated medical implant being received in the stop plug, the end of the elongated medical implant being adjacent the end wall of the stop plug, the end wall of the stop plug forming a barrier to translation of the elongated medical product along the longitudinal axis toward the end wall, wherein the stop plug includes a top lug extending upwardly from the stop plug and wherein the combination further comprises a retainer closing the open top of the cavity, the retainer having a slot engaging the top lug of the stop plug.

* * * * *